US007751611B2

(12) United States Patent
Akiyama et al.

(10) Patent No.: US 7,751,611 B2
(45) Date of Patent: Jul. 6, 2010

(54) APPARATUS FOR INSPECTING APPEARANCE OF INSPECTION PIECE

(75) Inventors: Yoshihiro Akiyama, Tokyo (JP); Yong Yang, Tokyo (JP); Sakie Akiyama, Tokyo (JP)

(73) Assignee: Saki Corporation, Tokyo (JP)

( * ) Notice: Subject to any disclaimer, the term of this patent is extended or adjusted under 35 U.S.C. 154(b) by 932 days.

(21) Appl. No.: 11/314,094

(22) Filed: Dec. 22, 2005

(65) Prior Publication Data

US 2006/0165274 A1 Jul. 27, 2006

(30) Foreign Application Priority Data

Dec. 24, 2004 (JP) ............................ 2004-373741

(51) Int. Cl.
*G06K 9/00* (2006.01)

(52) U.S. Cl. ......................... 382/147; 29/740; 382/152

(58) Field of Classification Search ................ 382/143, 382/144, 145, 147, 152
See application file for complete search history.

(56) References Cited

U.S. PATENT DOCUMENTS 4,538,909 A * 9/1985 Bible et al. .............. 356/239.1
4,759,074 A * 7/1988 Iadipaolo et al. ............ 382/152
4,884,696 A * 12/1989 Peleg ......................... 209/545
5,161,202 A * 11/1992 Kitakado et al. ............ 382/147
5,230,027 A * 7/1993 Kikuchi ...................... 382/147
5,835,223 A * 11/1998 Zwemer et al. ............. 356/600
5,978,521 A * 11/1999 Wallack et al. .............. 382/294
6,061,086 A * 5/2000 Reimer et al. ............... 348/125
6,064,757 A * 5/2000 Beaty et al. ................. 382/147
6,072,898 A * 6/2000 Beaty et al. ................. 382/146
6,122,065 A * 9/2000 Gauthier ..................... 356/394
6,173,071 B1 * 1/2001 Wasserman et al. ......... 382/147
6,484,066 B1 * 11/2002 Riess et al. ................. 700/217
6,493,597 B1 * 12/2002 Linares et al. ................ 700/83

(Continued)

FOREIGN PATENT DOCUMENTS

JP 11-118439 4/1999

(Continued)

OTHER PUBLICATIONS

English Abstract of JP Application 2001-084244, Publication No. 2003-115047, Apr. 18, 2003, Patent Abstracts of Japan, Japanese Patent Office Website.

(Continued)

*Primary Examiner*—Gregory M Desire
(74) *Attorney, Agent, or Firm*—Ralph A Dowell; Neil Henderson

(57) ABSTRACT

An appearance inspection apparatus for inspecting a board is provided with multiple imaging units for capturing respective images of the board. Multiple slave personal computers respectively provided for the multiple imaging units inspect the board by referring to data of images of the board captured by the respective imaging units. Each of the multiple slave personal computers transmits, to other slave personal computers, shared data that are necessary for inspection by other slave personal computers. The shared data is acquired by each of the slave personal computers from data of an image of the inspection piece captured by an associated imaging unit. Each of the slave personal computers inspects an appearance of the board by referring to the shared data received from another slave personal computer.

6 Claims, 6 Drawing Sheets

U.S. PATENT DOCUMENTS

| | | | | |
|---|---|---|---|---|
| 6,621,566 | B1 * | 9/2003 | Aldrich et al. | 356/237.1 |
| 6,667,762 | B1 * | 12/2003 | Bouvier et al. | 348/92 |
| 6,753,896 | B2 * | 6/2004 | Shirota et al. | 347/236 |
| 6,831,998 | B1 * | 12/2004 | Koshishiba et al. | 382/147 |
| 6,914,678 | B1 * | 7/2005 | Ulrichsen et al. | 356/429 |
| 6,915,006 | B2 * | 7/2005 | Beaty et al. | 382/145 |
| 7,002,676 | B2 * | 2/2006 | Akiyama | 356/237.2 |
| 7,010,086 | B2 * | 3/2006 | Chopra | 378/22 |
| 7,079,678 | B2 * | 7/2006 | Beaty et al. | 382/145 |
| 7,085,411 | B2 * | 8/2006 | Beaty et al. | 382/154 |
| 7,215,808 | B2 * | 5/2007 | Miller | 382/145 |
| 7,221,443 | B2 * | 5/2007 | Akiyama | 356/237.1 |
| 7,375,360 | B2 * | 5/2008 | Kim | 250/559.05 |
| 2004/0212797 | A1 * | 10/2004 | Akiyama | 356/237.5 |
| 2004/0218040 | A1 * | 11/2004 | Akiyama | 348/92 |
| 2005/0157841 | A1 * | 7/2005 | Chopra | 378/22 |
| 2006/0165273 | A1 * | 7/2006 | Akiyama | 382/145 |
| 2007/0230819 | A1 * | 10/2007 | Shimizu | 382/275 |
| 2008/0156207 | A1 * | 7/2008 | Ellenbogen | 101/126 |

FOREIGN PATENT DOCUMENTS

| | | |
|---|---|---|
| JP | 11-132966 | 5/1999 |
| JP | 2003-115047 | 4/2003 |

OTHER PUBLICATIONS

English Abstract of JP Application 09-278382, Publication No. 11-118439, Apr. 30, 1999, Patent Abstracts of Japan, Japanese Patent Office Website.

State Intellectual Property Office of People's Republic of China, The First Office Action, Feb. 1, 2008, Application No. 200510003383.9.

Japanese Patent Office, Patent Application No. 2004-373741, Notification of Reason(s) for Refusal, Apr. 20, 2010.

English Abstract of JP Application 09-300978, Publication No. 11-123966, May 21, 2005, Patent Abstracts of Japan, Japanese Patent Office Website.

* cited by examiner

APPARATUS FOR INSPECTING APPEARANCE OF INSPECTION PIECE

BACKGROUND OF THE INVENTION

1. Field of the Invention

The present invention relates to a technology for inspecting the appearance of an inspection piece and, more particularly, to a technology for inspecting the appearance of a package board by using multiple imaging means.

2. Description of the Related Art

Recently, electronic boards are used in a vast majority of equipment. Miniaturization, slim size and low price are persistent goals to be achieved in equipment in which electronic boards are used. For this purposes, high-integration design is practiced. Elements essential to achieve high-integration design include high-density packaging technology as well as availability of various design tools and advancement in semiconductor technology. Fabrication technology and inspection technology are important considerations to achieve high-density packaging. There is proposed a technology of using image recognition technology to inspect a printed board (hereinafter, referred to as a "board") on which components are already mounted.

For example, patent document No. 1 proposes a technology adapted to a high-definition image generating apparatus for use in the field of computer graphics in which multiple inexpensive personal computers and low-resolution display apparatuses are combined. The technology enables high-definition images to be presented efficiently by distributing the workload of image generation over the individual personal computers. Further, patent document No. 2 proposes a package board appearance inspection system provided with a final result output means for outputting a final result of inspection of a package board to a management computer.

[patent document No. 1]

JP 2003-115047 A

[patent document No. 2]

JP 11-118439

While technologies are proposed for using image recognition technology to inspect a board, there is a demand for an appearance inspection apparatus characterized by high expandability and flexible system structure. Also demanded are reduction in time required to inspect a board and improvement in precision with which to inspect a board. The technology described above does not propose an appearance inspection apparatus in which an independent personal computer is capable of making a determination on its own without requiring a controller for overall control. As such, it does not achieve a system structure which is highly expandable and flexible. With the current status of technology, an extended period of time is required if inspection depends on the recognition of a high-definition image. If inspection time is reduced, inspection precision cannot be improved.

SUMMARY OF THE INVENTION

Accordingly, a primary purpose of the present invention is to enable a highly expandable and flexible system structure of an appearance inspection apparatus, to reduce time required for inspection of a board or the like or to improve inspection precision.

In one embodiment of the present invention, an appearance inspection apparatus comprises: a plurality of imaging units which capture respective images of an inspection piece; a plurality of inspecting means which are respectively provided for the plurality of imaging units and which inspect the inspection piece by referring to data of the images captured by the respective imaging units. Each of the inspecting means transmits, to other inspecting means, shared data necessary for inspection by other inspecting means. According to this embodiment, a highly expandable and flexible appearance inspection apparatus for inspecting an inspection piece is achieved. Moreover, time require to inspect an inspection piece such as a board is reduced and inspection precision is improved.

The shared data may be acquired by the inspecting means from data of images of the inspection piece captured by the respective imaging units. According to this embodiment, it is not necessary to input shared data to the inspection apparatus by other means so that inspection efficiency is improved.

Each of the inspecting means inspects an appearance of the inspection piece by referring to the shared data received from another inspecting means. According to this embodiment, it is not necessary to input shared data to the inspection apparatus by other means so that inspection efficiency is improved.

According to the inventive appearance inspection apparatus, a highly expandable and flexible system structure is achieved by allowing independent personal computers to make a determination on their own without requiring a controller for overall control. Moreover, time required to inspect an inspection piece such as a board is reduced and inspection precision is improved.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which.

DETAILED DESCRIPTION OF THE INVENTION

A description will now be given of an embodiment of the present invention with reference to the attached drawings.

Figure 1:
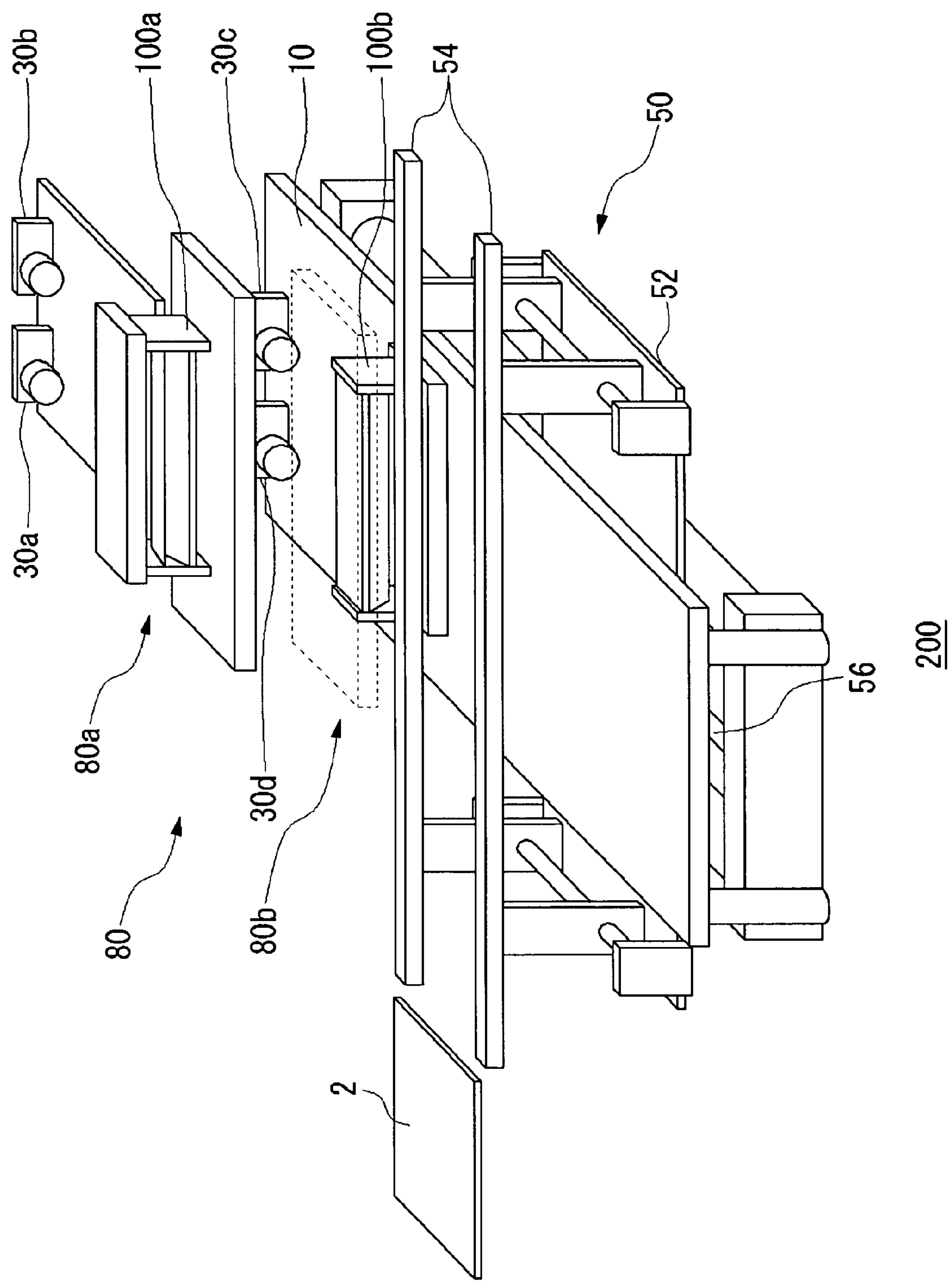
FIG. 1 shows the structure of an appearance inspection apparatus according to an embodiment of the present invention.

FIG. 1 shows the structure of an appearance inspection apparatus 200. The appearance inspection apparatus 200 is provided with an inspection table 10, a board transport table 50 and an imaging system 80. The board transport table 50 is provided with a support plate 52, two transport rails 54 and the like. The transport rails 54 are supported by the support plate 52.

Each of the transport rails 54 is provided with a transport belt for transporting a board 2 by driving a motor. The transport rails 54 transport the board 2 mounted on the transport belts to a position substantially aligned with the center of the inspection table 10. A transport sensor using a noncontact sensor such as an optical sensor (not shown) for detecting the board 2 transported is provided above the transport rails 54 and practically at the center of the inspection table. When the transport sensor detects an end of the board 2 or a detection hole provided in the board 2, it is determined that the board 2 is transported to a position substantially aligned with the center of the inspection table 10, whereupon the transportation of the board 2 by the transport belts is halted.

The board transport table 50 provided with the support plate 52 and the transport rails 54 is provided with an insertion unit inserted into a support shaft provided in the lower part of the appearance inspection apparatus 200. Thus, the board transport table 50 is supported so as to be movable in a direction perpendicular to the direction in which the transport rails 54 transport the board 2. By driving a ball screw 56 underneath the board transport table 50 into rotation with a motor, the board transport table 50 is moved to transport the board 2 as far as the imaging system 80. The front transport rail 54 as illustrated in FIG. 1 is provided with a clamp for correcting the configuration of the board 2 by pressing downward the board 2 mounted on the transport rail 54. The clamp corrects the deformation of the board 2 transported to a position substantially aligned with the center of the inspection table 10 before the board 2 is transported as far as the imaging system 80.

The imaging system 80 is provided with an upper imaging system **80*a* and a lower imaging system 80*b*. The upper imaging system 80*a* comprises an upper illuminating unit 100*a*, a first imaging unit 30*a*, a second imaging unit 30*b* and the like. The lower imaging system 80*b* comprises a lower illuminating unit 100*b*, a third imaging unit 30*c*, a fourth imaging unit 30*d* and the like. (Hereinafter, the upper illuminating unit 100*a* and the lower illuminating unit 100*b* will generically be referred to as illuminating units 100. The first imaging unit 30*a*, the second imaging unit 30*b*, the third imaging unit 30*c* and the fourth imaging unit 30*d* will generically be referred to as imaging units 30**).

When the board 2 is transported by the board transport table 50 as far as the imaging system 80, the board 2 is illuminated by the illuminating units 100 so that the imaging units 30 capture images of the surfaces of the board 2. The upper imaging system **80*a* is provided above the transport rails 54. The lower imaging system 80*b* is provided below the transport rails 54 so as to sandwich the board 2 (inspection piece) with the upper imaging system 80*a*. The transportation of the board 2 between the upper imaging system 80*a* and the lower imaging system 80*b* is controlled in coordination with the illumination of the board 2 by the illuminating units 100 and the imaging of the surfaces of the board 2 by the imaging units 30. This allows an image to be captured of the board 2 as the board 2 is transported by the board transport table 50 between the upper imaging system 80*a* and the lower imaging system 80*b*. The upper imaging system 80*a* can complete a process of capturing an image of one surface of the board 2 and the lower imaging system 80*b* can complete a process of capturing an image of the other surface of the board 2** in a single board transportation process. The term "single transportation process" may refer to a process whereby the board is transported in one direction only or a process whereby the board reciprocates.

When the imaging system 80 finishes capturing images of the surfaces of the board 2, the ball screw 56 is rotated so that the board transport table 50 is moved to a position that occurred when the transportation of the board 2 by the transport rails 54 is halted, whereupon the board 2 inspected is transported to a subsequent process. If another board 2 needs inspection, the board 2 is transported as described above by the transport rails 54 to a position substantially aligned with the center of the inspection table so that images are captured of the board 2.

Figure 2:
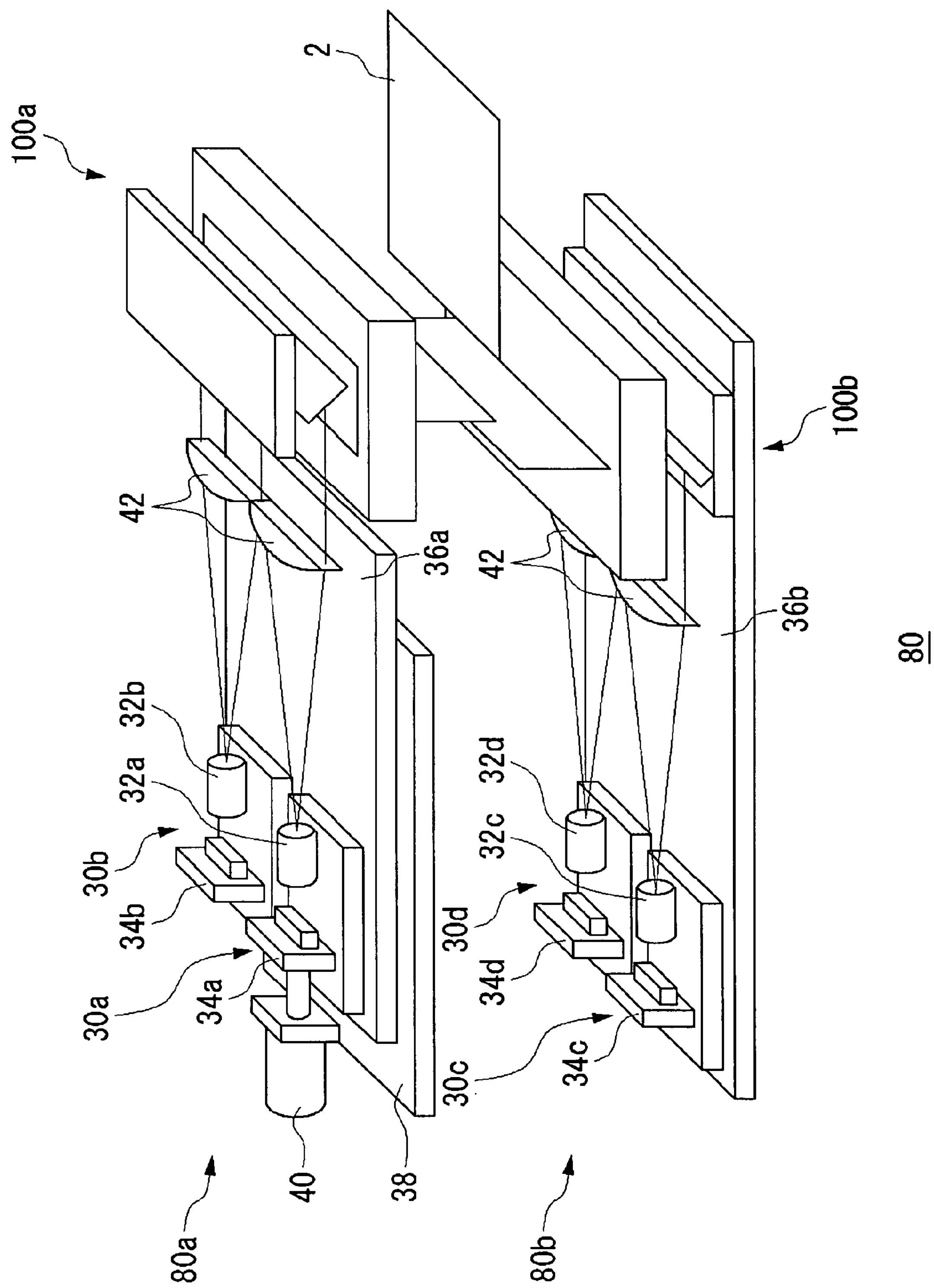
FIG. 2 shows the structure of an imaging system according to the embodiment.

FIG. 2 shows the structure of the imaging system 80 according to the embodiment. In the embodiment, the inspected surface of the board 2 is scanned by a licenser so as to form an image. A determination is then made as to whether components are mounted properly by image recognition. By feeding a control signal to the motor so as to move the board transport table 50 and transport the board 2 in a direction perpendicular to the direction of scan by the licenser, line-by-line images are obtained successively, allowing scanning to be completed in one-dimensional movement of the board 2. In some related-art appearance inspection apparatuses, the inspected surface is made to travel in two dimensions and is then halted, which steps are repeated for successive spot images to be taken. Such an approach generally requires a complex mechanism and a long period of time for inspection. In this respect, the use of a licenser as proposed in this embodiment is advantageous.

The upper imaging system 80 comprises an upper illuminating unit **100*a*, an upper frame 36*a*, an upper support frame 38, a first imaging unit 30*a*, a second imaging unit 30*b*, a motor 40, an intermediate lens 42 and the like. The lower imaging system 80*b* comprises a lower illuminating unit 100*b*, a lower frame 36*b*, a third imaging unit 30*c*, a fourth imaging unit 30*d*, an intermediate lens 42** and the like.

The first imaging lens **30*a*, the second imaging unit 30*b* and the intermediate lens 42 are permanently mounted on the upper frame 36*a*. The first imaging unit 30*a* comprises a first lens 32*a* and a first licenser 34*a*. The second imaging unit 30*b* comprises a second lens 32*b* and a second licenser 34*b*. By providing multiple imaging units 30 to capture an image of one surface of the board, an image of the board 2** can be captured with a high resolution. Therefore, inspection precision is improved. Inspection speed is also improved since a captured image is subject to distributed image processing.

The upper frame **36*a* is supported by the upper support frame 38 so as to be slidable in a direction in which the board 2 is transported. The upper frame 36*a* is driven by the motor 40 to slide with respect to the upper support frame 38. An imaging control unit for controlling imaging of the board feeds a control signal to the motor 40 in accordance with preset data on the thickness of the board, so as to slide the upper frame 36*a* with respect to the upper support frame 38. In this way, focus is achieved to capture an image of the top surface of the board 2**.

In the imaging system **80*a*, the first imaging unit 30*a* and the second imaging unit 30*b* are provided side by side and opposite to one surface of the board 2 in order to share the task of imaging the surface of the board 2. Arrangement of the first lens 32*a*, the first licenser 34*a*, the second lens 32*b*, the second licenser 34*b* and the intermediate lens 42 is determined such that the imaging ranges of the first imaging unit 30*a* and the second imaging unit 30*b* overlap to ensure that components on the board 2 located between the ranges are inspected. Similarly, the third imaging unit 30*c* and the fourth imaging unit 30*d* in the lower imaging system 80*b* are provided side by side and opposite to the other surface of the board 2 so as to capture an image of the other surface of the board 2. Arrangement of the third lens 32*c*, the third licenser 34*c*, the fourth lens 32*d*, the fourth licenser 34*d* and the intermediate lens 42 is determined such that the imaging ranges of the third imaging unit 30*c* and the fourth imaging unit 30*d* overlap. A pair comprising the first imaging unit 30*a* and the second imaging unit 30*b* and a pair comprising the third imaging unit 30*c* and the fourth imaging unit 30*d* are provided to sandwich the board 2 so that an image is captured of both surfaces of the board 2 in a single step of relative movement occurring between the imaging units and the substrate 2**.

To suppress blooming due to mutual optical interference, the upper illuminating unit 100*a* is provided toward the upstream in the direction in which the board is transported with respect to the lower illuminating unit 100*b*. Therefore, the board 2 transported by the board transport table 50 is moved to a start position within the scanning range of the first licenser 34*a* and the second licenser 34*b*. Subsequently, as the licensers 34 finish scanning one line on the board 2, a control signal is supplied to the motor driving the ball screw 56 so as to advance the board 2 by one line. By allowing the licensers 34 to scan the entire length of the board 2 in the direction in which the board 2 is transported, imaging of both surfaces of the board 2 is completed in a single board transportation process.

Figure 3:
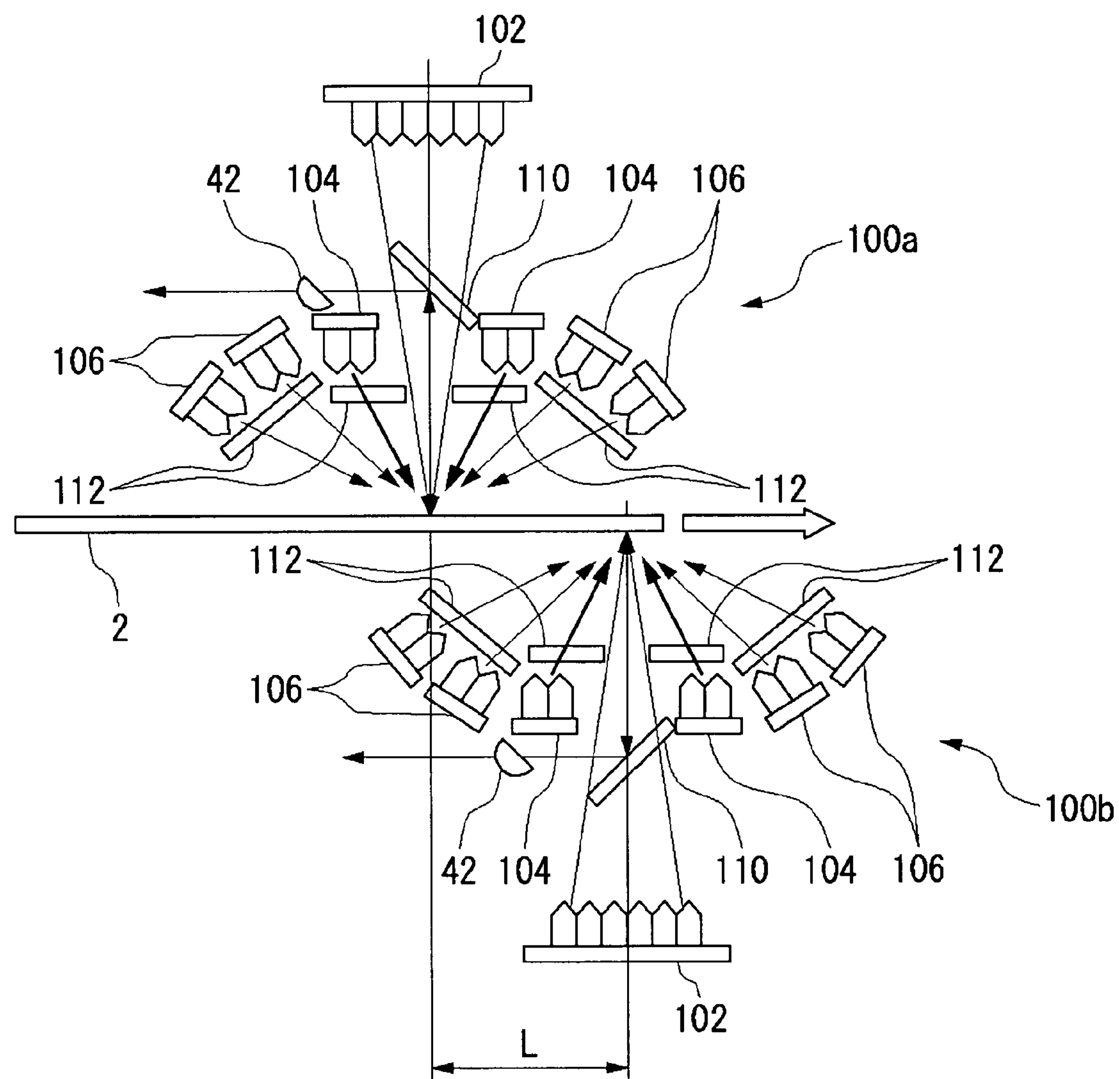
FIG. 3 shows the structure of an illuminating unit according to the embodiment.

FIG. 3 shows the structure of the illuminating units 100 according to the embodiment. The illuminating units 100 comprise the upper illuminating unit 100*a* and the lower illuminating unit 100*b*. Each of the upper illuminating unit 100*a* and the lower illuminating unit 100*b* comprises a first light source 102, a second light source 104, a third light source 106, a half mirror 110, an acrylic sheet 112 and the like. The first light source 102, the second light source 104 and the third light source 106 are arranged to surround the half mirror 110.

The first light source 102 comprises a group of light emitting diodes (LED) arranged in the scanning direction of the licensers 34 so as to extend longer than the length of the board 2. The first light source 102 is provided immediately above a scanned line on the board 2 scanned by the licensers 34 for incident illumination of the board 2 below. In this embodiment, the first light source 102 comprises a group of LEDs provided on a board parallel to the board 2. For efficient incident illumination of a scanned line for inspection, the board populated with the LED group may be divided in the middle into two sub-boards each of which carries a group of LEDs arranged in the scanning direction. By using the first light source 102 for incident illumination of the board 2 and detecting the light by the licensers 34, displacement of components, missing components and solder wetting characteristics on the board 2 can be determined.

The second light source 104 comprises a group of LEDs provided on two separate boards provided parallel to the board 2 and arranged in the scanning direction of the licensers 34 so as to extend longer than the length of the board 2. The two boards populated with the LEDs are provided to sandwich a scanned line in the direction in which the board is transported so as not to interfere with incident illumination of the scanned line by the first light source.

Similarly to the second light source 104, the third light source 106 also comprises a group of LEDs provided on two separate boards provided parallel to the board 2 and arranged in the scanning direction of the licensers 34 so as to extend longer than the length of the board 2. The two boards populated with LEDs are provided to sandwich a scanned line in the direction in which the board is transported so as not to interfere with the illumination of the scanned line by the first light source and the second light source. By using the second light source 104 for edge illumination of the board 2 and detecting the light by the licensers 34, occurrence of solder bridges, wrongly mounted components, reversal in polarity can be determined.

The first light source 102 emits green light, the second light source 104 emits white light and the third light source 106 emits blue light. The light sources illuminate the board 2 at different angles of incidence. Thus, the illuminating units 100 function as a composite light source illuminating the board 2 at multiple angles of incidence. The first light source 102 is designed to emit green light and the third light source 106 is designed to emit blue light because, due to progress in the LED technology in recent years, a green LED and a blue LED are brighter than a white LED and provide a clear image with a high S/N ratio. Since a majority of printed boards are green in color, the first light source is designed to emit green light for bright incident illumination on the plane. Characters printed by laser on the body of an IC or a chip are easily recognizable by illuminating them with blue light at a low angle. Therefore, the third light source 106 is designed to emit blue light.

The angle of incidence of light emitted by the first light source 102 and incident on the inspected surface of the board 2 via the half mirror 110 is substantially zero. In this embodiment, the first light source 102 is designed to provide a certain beam width, ensuring that some light components are incident on the board 2 at an angle of incidence of zero, even if the board 2 is warped. Light reflected from a scanned line is reflected by the half mirror 110 and is transmitted through the intermediate lens 42 before being incident on the lens 32.

The acrylic sheet 112 is provided between the second light source 104 and a scanned line and between the third light source 106 and the scanned line. The acrylic sheet 112 diffuses light from the second light source 104 and the third light source 106. Since each of the second light source 104 and the third light source 106 comprises a set of LEDs as point light sources, a spot light may present itself a reflected image without the diffusive action and may adversely affect inspection precision.

In this embodiment, the second light 104 emitting while light, the first light source 102 emitting green light and the third light source 106 emitting blue light are driven independently in the stated order so as to illuminate a scanned line three times. In each illumination, the licensers 34 scan the board 2. In this way, images of the board 2 illuminated by the light sources are obtained.

Light from one of the illuminating units 100 may leak at an end of the board 2 to the other of the illuminating units 100. There may be holes provided in the board 2 or holes may remain unfilled with solder. Light may also leak through these holes to the other of the illuminating units 100. In case light leaked to the other of the illuminating units 100 is directly scanned by the licensers 34, a phenomenon called blooming occurs, which may adversely affect imaging of the board 2. Therefore, the upper illuminating unit 100*a* and the lower illuminating unit 100*b* in this embodiment are provided with an offset of L with respect to each other in the direction in which the board is transported. The offset L may preferably be 50 mm or longer in respect of suppression of blooming.

Figure 4:
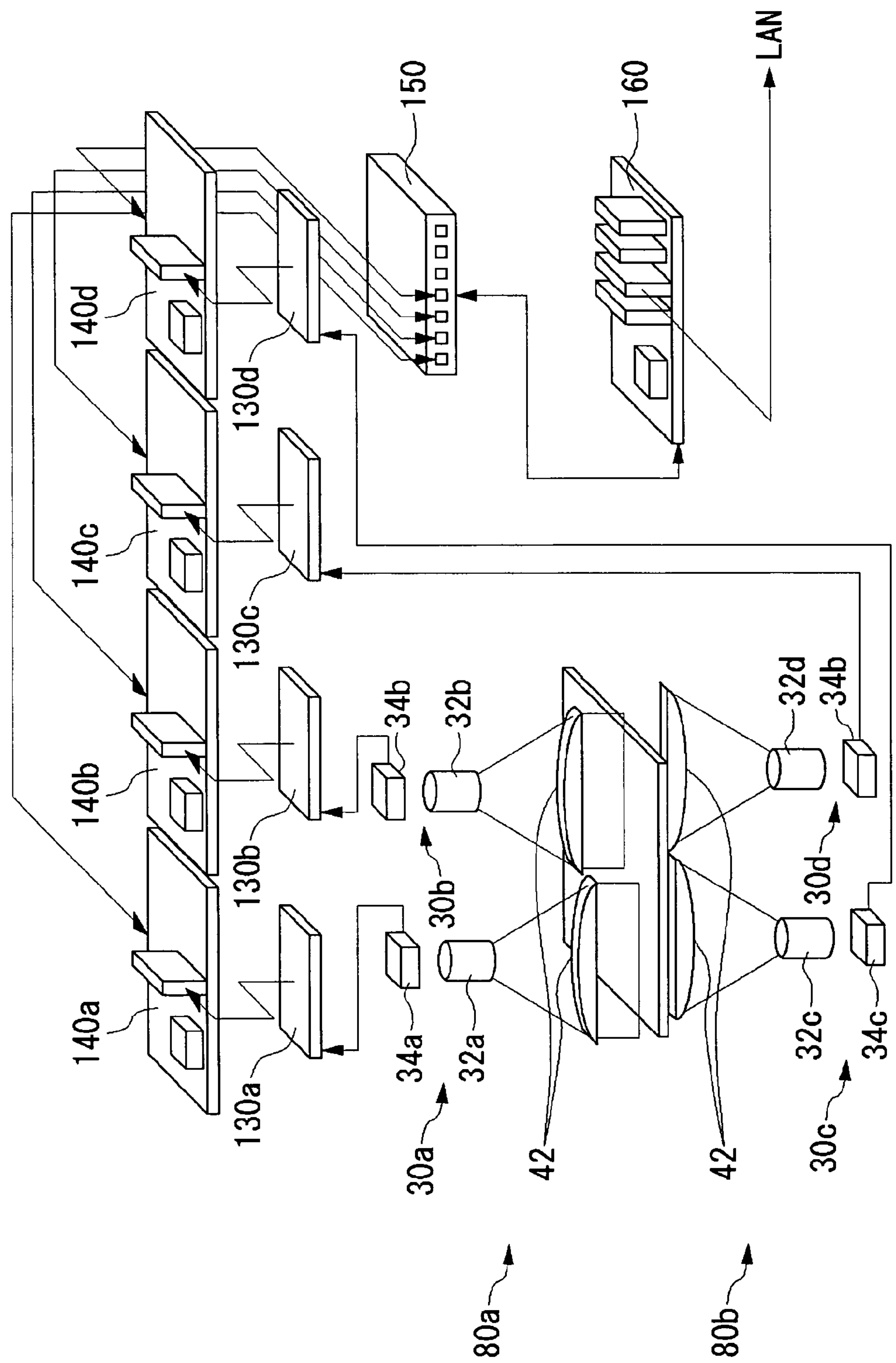
FIG. 4 shows the structure of an appearance inspection apparatus according to the embodiment in which slave personal computers as inspection units are included.

FIG. 4 shows the structure of an appearance inspection apparatus according to the embodiment in which slave personal computers 140 as inspection units are included. The upper imaging system 80*a* comprises the first imaging unit 30*a* and the second imaging unit 30*b*. The first imaging unit 30*a* corresponds to a first image processing unit 130*a* and a first slave personal computer (PC) 140*a* (inspection unit). The second imaging unit 30*b* corresponds to a second image processing unit 130*b* and a second slave PC 140*b*. Similarly, the lower imaging system 80*b* comprises the third imaging unit 30*c* and the fourth imaging unit 30*d*. The third imaging unit 30*c* corresponds to a third image processing unit 130*c* and a third slave PC 140*c*. The fourth imaging unit 30*d* corresponds to a fourth image processing unit 130*d* and a fourth slave PC

140*d* (hereinafter, the first image processing unit 130*a*, the second image processing unit 130*b*, the third image processing unit 130*c* and the fourth image processing unit 130*d* will generically be referred to as image processing units 130. The first slave PC 1401, the second slave PC 140*b*, the third slave PC 140*c* and the fourth slave PC 140*d* will generically be referred to as slave PCs 140).

Each of the slave PCs 140 is connected to the other slave PCs 140 via a switching hub 150 so that data exchange over a network is enabled. The slave PCs 140 are also connected to a master PC 160 as a managing unit. The master PC 160 is also connected to a local area network (LAN) and is capable of transmitting results of inspection to the other PCs connected to the LAN.

Images obtained as a result of the scanning by the licensers 34 of the imaging units 30 are transmitted to the image processing units 130 respectively corresponding to the imaging units 30. The image processing units 130 process the transmitted images and feed processed images to the respective slave PCs 140.

Each of the slave PCs 140 is provided with an image input board for receiving an image, a memory for storing image data and the like, a central processing unit (CPU) for inspecting the appearance of the board 2 by image recognition, and the like. Each of the image processing units 130 feeds an image to the corresponding image input board. Each of the slave PCs 140 supplied with the image stores the image in the memory and analyzes the image so as to acquire shared data including identification mark, bar code and other data that are necessary for inspection. Each of the slave PCs 140 acquiring the shared data transmits the shared data to the other slave PCs 140. The slave PCs receiving the shared data refer to the shared data so as to inspect the board 2. Thus, the slave PCs are capable of inspecting the board on their own.

The process described above is analogous to the workings of a cell inside a living organism. The cells have identical genes and select only those instructions related to them for execution, in accordance with a trigger. Analogy can be drawn between the genes and inspection according to this embodiment and between the cells and the slave PCs 140. In the related art, the master PC 160 is solely responsible for assigning inspection locations and inspection menus to multiple image processing boards. By allowing the slave PCs 140 to share the same inspection data and to select only those data portions related to them for execution, a highly expandable and flexible system structure of an appearance inspection apparatus is achieved, inspection precision is improved and inspection time is reduced.

Figure 5:
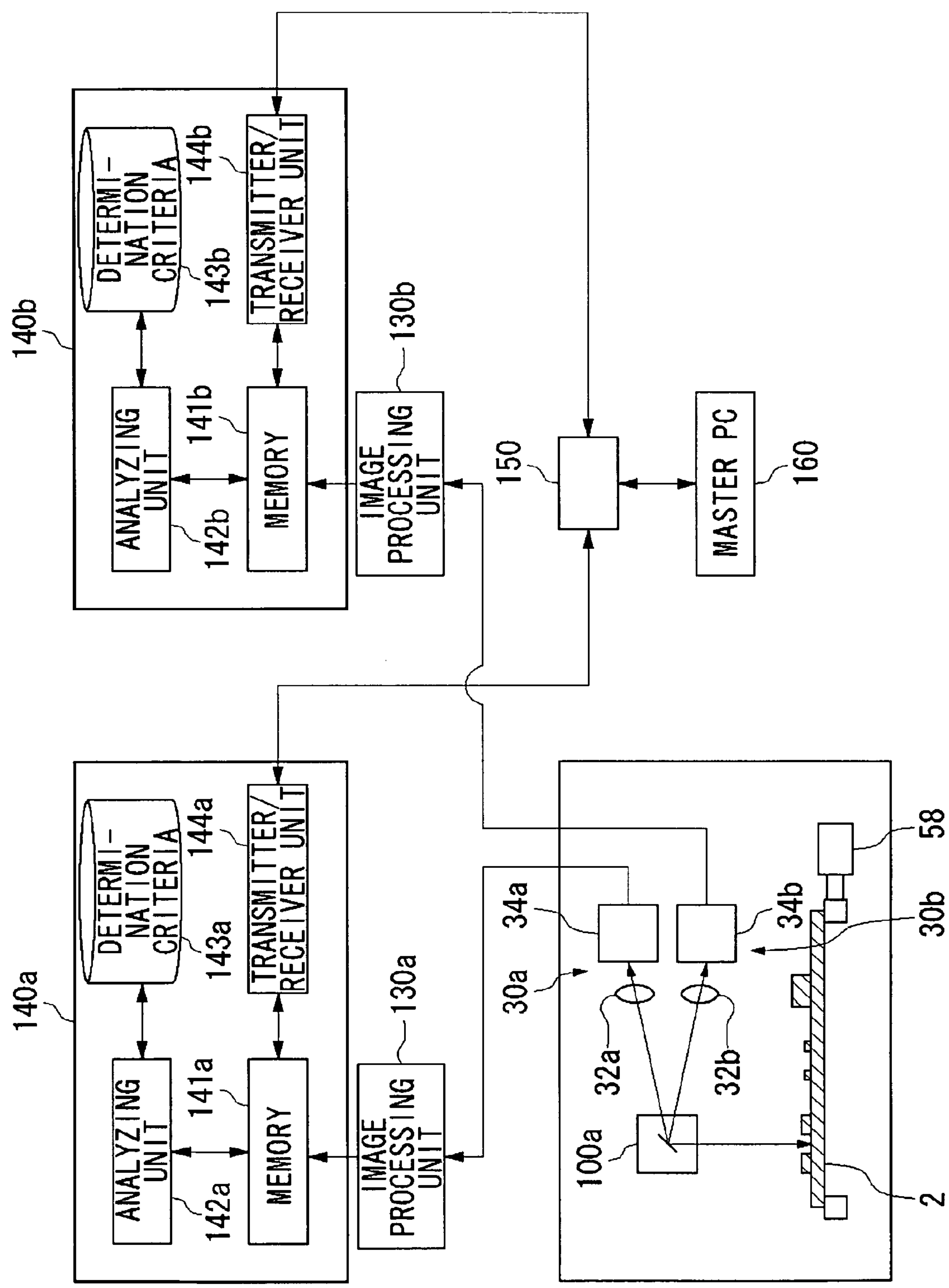
FIG. 5 is a schematic view showing the structure of an appearance inspection apparatus according to the embodiment.

FIG. 5 is a schematic view showing the structure of an appearance inspection apparatus according to the embodiment. The structure of the first imaging unit 30*a* and the second imaging unit 30*b* of the upper imaging system and that of the first slave PC 140*a* and the second slave PC 140*b* associated therewith is illustrated in FIG. 5. The illustration is also applicable to the structure of the third imaging unit 30*c* and the fourth imaging unit 30*d* of the lower imaging system and that of the third slave PC 140*c* and the fourth slave PC 140*d* associated therewith. The illustration is also applicable to data exchange between the upper and lower slave PCs 140 (for example, between the first slave PC 140*a* and the third slave PC 140*c*).

When the board 2 is illuminated by the upper illuminating unit 100*a*, the first licenser 34*a* of the first imaging unit 30*a* scans the board 2 through the first lens 32*a*. The second licenser 34*b* of the second imaging unit 30*b* scans through the second lens 32*b*. When a line of image is obtained by scanning, a control signal is input to the motor 58 so as to move the board 2 by one line.

The scanned image obtained by the first imaging unit 30*a* is transmitted to the first image processing unit 130*a* and the image obtained by the second imaging unit 30*b* is transmitted to the second image processing unit 130*b*. Each of the image processing units 130 processes the received image. The first image processing unit 130*a* transmits the processed image to a memory 141*a* of the first slave PC 140*a* and stores the image therein. The second image processing unit 130*b* transmits the processed image to a memory 141*b* of the second slave PC 140*b* and stores the image therein.

The analyzing unit 142 (a generic reference to each of analyzing units in the slave PCs 140) in each of the slave PCs 140 refers to the image stored in an associated memory 141 (a generic reference to the memory provided in each of the slave PC 140*s*) so as to analyze shared data necessary for inspection of the board 2 in the other slave PCs 140. The shared data include positional data in an identification mark indicating the position of the board 2, identification data such as the serial number and the fabrication date of the board 2 obtained by analyzing the identification mark such as a bar code provided in the board 2, images of components captured both by the first imaging unit 30*a* and the second imaging unit 30*b*, as well as other data necessary for inspection of the board 2.

When the analyzing unit 142 has acquired shared data necessary for inspection of the board 2 by analyzing the image, the analyzing unit 142 stores the shared data in the memory 141 and transmits the shared data to the other slave PCs 140. While FIG. 5 shows only the first slave PC 140*a* and the second slave PC 140*b*, the slave PCs 140, including the third slave PC 140*c* and the fourth slave PC 140*d*, exchange shared data with each other.

The analyzing unit 142 of the slave PC 140 receiving the shared data refers to the received shared data so as to analyze the image stored in the memory 141 and inspects the board 2 in accordance with determination criteria stored in a determination criteria storage unit 143. Thus, the slave PCs can share the data in a system wherein the multiple imaging units 30 capture images of the board 2 and the slave PCs 140 provided for the respective imaging units inspect the board 2. Therefore, a highly expandable and flexible system structure of an appearance inspection apparatus is achieved, precision in inspection of the board is improved and inspection time is reduced.

The images of the board 2, the shared data including the positional data in an identification mark and the like, and the results of inspection of the board 2 by the slave PCs 140 are stored in the memories of the slave PCs and transmitted to the master PC 160. The master PC allows screen display of error locations of the board 2 as necessary, in accordance with the images of the board 2 and the results of inspection of the board 2.

Figure 6A:
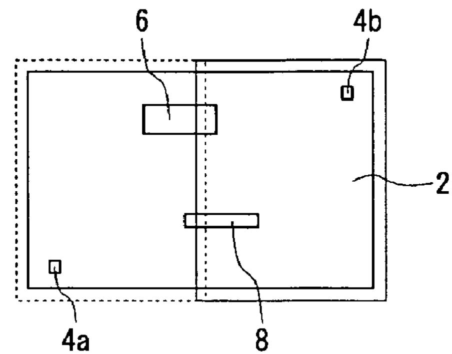
FIG. 6A shows imaging ranges on a board.
Figure 6B:
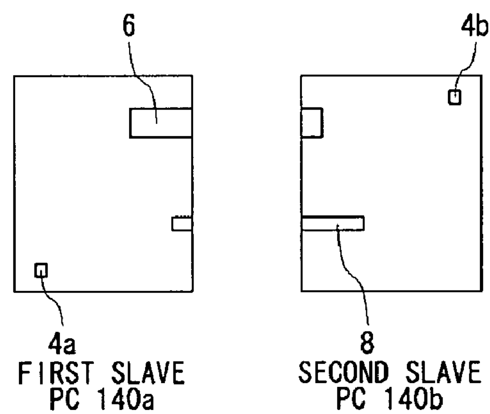
FIG. 6B shows images of a board captured.
Figure 6C:
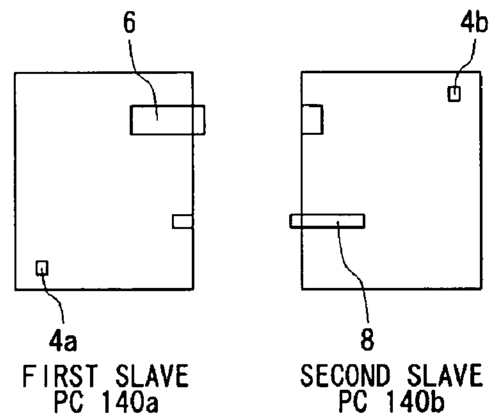
FIG. 6C shows images of a board incorporating data related to components for inspection.

FIG. 6A shows imaging ranges on the board 2; FIG. 6B shows images of the board 2 captured; and FIG. 6C shows images of the board 2 incorporating data related to components for inspection. While only one surface of the board 2 is illustrated, the description referring to these figures also concerns the other surface of the board 2.

Referring to FIG. 6A, the first imaging unit 30*a* is responsible for capturing an image of the left side of the board 2 and the second imaging unit 30*b* is responsible for capturing an image of the right side of the board 2. An overlapping imaging range is provided between the imaging range of the first imaging unit 30*a* and the imaging range of the second imaging unit 30*b* so as not to create a range of missing images between the imaging ranges.

The board 2 is provided with a first identification mark 4*a* and a second identification mark 4*b* indicating the position of the board. A first component 6 and a second component 8 are provided substantially at the center of the board 2 to extend across the imaging range of the first imaging unit 30*a* and the imaging range of the second imaging unit 30*b*. A bar code (not shown) storing the identification data of the board 2 is provided in the board 2.

Imaging of the board 2 by the first imaging unit 30*a* and the second imaging unit 30*b* is performed such that the first imaging unit 30*a* captures an image of the left side of the board 2 as illustrated in FIG. 6B and the second imaging unit 30*b* captures an image of the right side of the board 2 as illustrated in FIG. 6B. The image captured by the first imaging unit 30*a* is stored in the memory 141*a* of the first slave PC 140*a*. The image captured by the second imaging unit 30*b* is stored in the memory 141*b* of the second slave PC 140*b*. The first identification mark 4*a* and images of parts of the first component 6 and the second component 8 are captured by the first imaging unit 30*a* and stored in the memory 141*a* of the first slave PC 140*a*. The second identification mark 4*b* and mages of parts of the first component 6 and the second component 8 are captured by the second imaging unit 30*b* and stored in the memory 141*b* of the second slave PC 140*b*.

The analyzing unit 142 of each the salve PCs 140 analyzes the image stored in the memory 141 so as to retrieve the positional data in the identification mark from an image of the identification mark. The analyzing unit 142 also retrieves identification data such as the serial number and the fabrication date of the board 2 from an image of the bar code. The shared data including the identification data and the positional data in the identification mark are transmitted from a transmitter and receiver unit 144 (a generic reference to each of transmitter and receiver units provided in the slave PCs 140) to the other slave PCs 140. For example, the board 2 may be slightly inclined, or the board 2 may be displaced with respect to an ideal position in the scan direction or the transportation direction. Therefore, a PC responsible for inspecting the board needs to have accurate knowledge of the position and orientation of the board before inspecting the board. Each of the slave PCS 140 inspecting the board 2 according to the embodiment can have accurate knowledge of the position and orientation of the board 2 captured in images, by allowing the data such as the positional data in the identification mark to be shared between the slave PCs. This is essential in case an identification mark is not included in the imaging range of the imaging unit corresponding to the slave PC or if only some of the identification marks are included in the range. Accordingly, it is possible for multiple PCs to share the workload of inspecting the board 2. A highly expandable and flexible system structure of an appearance inspection apparatus is achieved, precision in inspecting the board 2 is improved, and inspection time is reduced.

As for components (for example, the first component 6 and the second component 8) provided on the board 2 to extend across the imaging ranges of multiple imaging units 30, the task of inspecting such a component is assigned to a selected one of the slave PCs 140 depending on which of the imaging units 30 provides an imaging range covering the center of the component. For example, the center of the first component 6 is located within the imaging range of the first imaging unit 30*a*. Therefore, the first slave PC 140*a* (inspection unit associated with the first imaging unit 30*a*) inspects the component 6. Conversely, the second component 8 is located with the imaging range of the second imaging unit 30*b*. Therefore, the second slave PC 140*b* (inspection unit associated with the second imaging unit 30*b*) inspects the component 8.

If the imaging units 30 merely capture respective images of the board 2 as shown in FIG. 6B, images of components such as the first component 6 and the second component 8 that are provided on the board to extend across the imaging ranges of the multiple imaging units 30 will contain missing parts. It is therefore necessary to acquire missing parts of the images from other slave PCs 140 which store the missing parts in the respective memories.

For example, when the first slave PC 140*a* receives the positional data in the second identification mark 4*b* from the second slave PC 140*b*, it allows the first slave PC 140*a* to compute the position and orientation of the image of the board 2 captured by the first imaging unit 30*a*, by referring to the positional data in the first identification mark 4*a* acquired by the first slave PC 140*a* itself and the positional data in the second identification mark 4*b* thus received. The first slave PC 140*a* is thus capable of recognizing the position and orientation of the image captured by the first imaging unit 30*a*. By recognizing the position and orientation of the image, the first slave PC 140*a* identifies an image of a part of the second component 8 to be transmitted to the second slave PC 140*b*. The first slave PC 140*a* thus transmits the image of a part of the second component 8 to the second slave PC 140*b*.

Similarly, when the second slave PC 140*b* receives the positional data in the first identification mark 4*a* from the first slave PC 140*a*, it allows the second slave PC 140*b* to compute the position and orientation of the image of the board 2 captured by the second imaging unit 30*b*, by referring to the positional data in the second identification mark 4*b* acquired by the second slave PC 140*b* itself and the positional data in the first identification mark 4*a* thus received. Thus, the second slave PC 140*b* is capable of recognizing the position and orientation of the image captured by the second imaging unit 30*b*. By recognizing the position and orientation of the image, the second slave PC 140*b* identifies an image of a part of the first component 6 to be transmitted to the first slave PC 140*a*. The first slave PC 140*a* transmits the image of a part of the second component 8 to the second slave PC 140*b*.

Thus, each of the slave PCs 140 can acquire the images of the entirety of the components of which the PC is responsible for inspection, by importing the missing parts of the images. Accordingly, all of the components on the board 2 can be inspected. Each of the slave PCs 140 inspects components of which the PC is responsible for inspection, in accordance with a determination criteria. When the inspection is complete, each of the slave PCs 140 transmits a result of inspection to the master PC 160.

It is to be understood that the invention is not limited by the embodiment as described above. It is also within the scope of the present invention to combine elements of the embodiment as appropriate. Modifications within the scope of the present invention such as design modifications can also be made to the embodiment on the basis of the knowledge of the skilled person. Some examples of such modifications will be described below.

Instead of scanning the board 2, the imaging units 30 may capture images of a selected range successively by using a CCD sensor or the like. According to this modification, images of the board 2 can be captured easily.

The shared data may be transmitted by each of the slave PCs 140 to the master PC 160 so that the master PC 160 may transmit the data to the other slave PCs 140. According to this modification, the master PC 16 can also enjoy the sharing of the shared data.

Only one imaging unit 30 and one associated slave PC 140 may be provided above the board 2 for inspection of one surface thereof, and one each may be provided below the board 2 for inspection of the other surface. In this case, the shared data is exchanged between the slave PC 140 for inspecting one surface of the board 2 and the slave PC 140 for inspecting the other surface. According to this modification, provision of an identification mark on one surface of the board 2 may be omitted and the inspection thereof may be performed by referring to the positional data provided on the other surface bearing an identification mark. As a result, the structure of the board 2 is simplified.

The board 2 may be fixed and the illuminating units 100 and the imaging units 30 may be moved instead. According to this modification, the board 2 is held in a stable manner while an image thereof is being captured.

While the preferred embodiments of the present invention have been described using specific terms, such description is for illustrative purposes only, and it is to be understood that changes and variations may be made without departing from the spirit or scope of the appended claims.

What is claimed is:

1. An appearance inspection apparatus comprising:

a plurality of imaging units which capture images of respectively different parts of an electronic board;

a plurality of inspecting means which are respectively provided for the plurality of imaging units and which inspect the condition of components in the electronic board as mounted by referring to data of the images of the electronic board captured by the respective imaging units, wherein each of the inspecting means stores different determination criteria associated with respective areas to be imaged by the respective imaging units and transmits, to other inspecting means, shared data necessary for inspection by other inspecting means, and the other inspecting means inspects how the components in the electronic board are mounted by referring to the shared data thus received and based on the determination criteria stored in the other inspecting means.

2. The appearance inspection apparatus according to claim 1, wherein the shared data are acquired by the inspecting means from data of images of the electronic board captured by the respective imaging units.

3. The appearance inspection apparatus according to claim 1, wherein each of the inspecting means inspects an appearance of the electronic board by referring to the shared data received from another inspecting means.

4. The appearance inspection apparatus according to claim 1, wherein each of the inspecting means transmits, to other inspecting means, positional data indicating the position of the electronic board imaged, as the shared data, and the other inspecting means inspects how the components in the electronic board are mounted by using the positional data thus received to have a knowledge of the position of the electronic board imaged.

5. The appearance inspection apparatus according to claim 1, wherein each of the inspection means transmits, to other inspecting means, identification data for identifying the electronic board imaged, as the shared data, and the other inspecting means inspects how the components in the electronic board are mounted by using the identification data thus received to identify the electronic board imaged.

6. The appearance inspection apparatus according to claim 1, wherein the plurality of imaging units capture images of the electronic board such that the imaging ranges of the units overlap, each of the inspecting means transmits, to other inspecting means, image data for the overlapping imaging ranges, as the shared data, and the other inspecting means inspects how the components in the electronic board are mounted, by using the image data for the overlapping imaging ranges thus received.

* * * * *